United States Patent [19]

Jacobi et al.

[11] 4,370,342

[45] Jan. 25, 1983

[54] S-ALKYL 3-ALKYLTHIOPROPIONOTHIOATE COMPOUNDS, THEIR PRODUCTION AND THEIR MEDICINAL USE

[75] Inventors: Haireddin Jacobi, Leichlingen; Wolfgang Opitz, Overath, both of Fed. Rep. of Germany

[73] Assignee: Troponwerke GmbH & Co. KG, Cologne, Fed. Rep. of Germany

[21] Appl. No.: 241,147

[22] Filed: Mar. 6, 1981

[30] Foreign Application Priority Data

Mar. 28, 1980 [DE] Fed. Rep. of Germany ....... 3012000

[51] Int. Cl.³ .................... A61K 31/38; A61K 31/44; C07C 153/00; C07D 333/24
[52] U.S. Cl. ................... 424/275; 424/263; 424/285; 424/301; 260/455 R; 549/59; 549/501; 546/261
[58] Field of Search ............ 260/455 R; 549/59, 501; 546/261; 424/275, 285, 263, 301

[56] References Cited

FOREIGN PATENT DOCUMENTS 2753768 2/1978 Fed. Rep. of Germany .

*Primary Examiner*—Alan Siegel
*Attorney, Agent, or Firm*—Sprung, Horn, Kramer & Woods

[57] ABSTRACT

The invention relates to S-alkyl 3-alkylthiopropionothioates of Formula (I) as defined herein. Also included in the invention are methods for the manufacture of said S-alkylthiopropionothioates, compositions containing them and the use of said compounds and compositions for the treatment of inflammatory processes.

17 Claims, No Drawings

S-ALKYL 3-ALKYLTHIOPROPIONOTHIOATE COMPOUNDS, THEIR PRODUCTION AND THEIR MEDICINAL USE

The present invention relates to certain new S-alkyl 3-alkylthiopropionothioate compounds, to a process for their production and to their use in medicaments for the treatment of inflammatory processes.

The pharmaceutical use of similar compounds has already been described in DT-OS (German Published Specification) 2,753,768 and in DT-OS (German Published Specification) 2,824,386. However, the extent to which the unsubstituted compounds claimed in the said specifications can be utilised is severely restricted because they have a very powerful odour.

According to the present invention there are provided compounds which are S-alkyl 3-alkylthiopropionothiates of the general formula

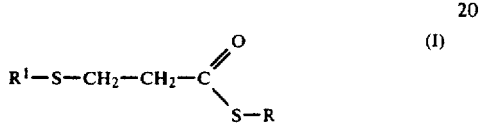

in which
R and R$^1$ are identical or different and each represents a substituted straight-chain or branched alkyl radical, which is substituted by amino, alkylamino, dialkylamino, aryl, aryloxy, or hetero-aryl, the said aryl and hetero-aryl radicals in turn being optionally substituted by 1, 2 or 3 identical or different substituents selected from halogen, alkyl, alkoxy, trifluoromethyl, nitro, aralkoxy or aryloxy, or represents a cyclic alkyl radical.

The straight-chain or branched alkyl radical mentioned in the definition of R and R$^1$ preferably represents a substituted alkyl radical with 1 to 10 and in particular 1 to 6 carbon atoms. The cyclic alkyl radical preferably represents a mono-, di-, tri- or tetra-cyclic alkyl radical with 5 to 10 carbon atoms, preferably a monocyclic alkyl radical with 4, especially 5 or 6, carbon atoms or a dicyclic alkyl radical with 8, 9 or especially 10 carbon atoms and particularly a tricyclodecane of the adamantane type. Aryl preferably represents mono or bi-cyclo carbocyclic aryl, such as phenyl, biphenyl or naphthyl. Halogen preferably represents chlorine or fluorine. Aryloxy preferably represents mono or bi-cyclic carbocyclic aryloxy, such as phenoxy bi-phenyloxy or naphthoxy.

Alkoxy preferably represents alkoxy with 1 to 4 carbon atoms. Hetero-aryl preferably represents a 5-membered to 6- or 7-membered ring which contains an oxygen, sulphur or nitrogen atom as the hetero-atom. Also included as heteroaryl are 5-membered to 6 or 7-membered rings which contain two alike or different hetero-atoms selected from oxygen, sulphur and nitrogen.

Compounds of particular interest are those of the formula (I) in which
R and R$^1$ are identical or different and each represents a substituted straight-chain or branched alkyl radical with 1 to 10 carbon atoms, the alkyl radical being substituted by amino or alkylamino or dialkylamino, each with 1 to 4 carbon atoms in their alkyl radicals, or by phenyl, naphthyl, pheoxy or naphthoxy, or by 5-membered to 7-membered hetero-aryl which contain an oxygen, sulphur or nitrogen atom as the hetero-atom, the said phenyl, phenoxy and hetero-aryl radicals being optionally substituted by 1, 2 or 3 identical or different substituents selected from halogen, trifluoromethyl, nitro, phenoxy, benzyloxy, alkyl with 1 to 4 carbon atoms or alkoxy with 1 to 4 carbon atoms, or represents a mono-, di-, tri- or tetra-cyclic alkyl radical with 5 to 10 carbon atoms. Compounds of especial interest are those of formula (I) in which
R and R$^1$ are identical or different and each represent a substituted straight-chain or branched alkyl radical with 1 to 6 carbon atoms or represent an adamantyl radical, the alkyl radical being substituted by amino or alkylamino or dialkylamino, each with 1 to 4 carbon atoms in the alkyl radicals, or by phenyl, naphthyl or phenoxy radicals or 5-membered to 6-membered hetero-aryl radicals which contain an oxygen, sulphur or nitrogen atom as the hetero-atom, the said phenyl and phenoxy radicals being optionally substituted by 1 or 2 identical or different substituents from the group comprising halogen, trifluoromethyl, nitro, benzyloxy or alkyl with 1 to 2 carbon atoms or alkoxy with 1 to 2 carbon atoms. S-(Adamant-1-yl) 3-(adamantyl-1-thio)-propionothioate is particularly preferred.

According to the present invention, there is further provided a process for the production of a compound of the present invention in which an acrylic acid derivative of the formula

in which
X represents a hydroxyl radical, a halogen, an acyloxy (particularly an alkanoyloxy) radical or an ester radical of the formula OR'
in which
R' denotes an optionally substituted alkyl, aryl or aralkyl radical,
is reacted with a mercaptan of the formula

in which
R and R$^1$ have the meanings indicated above, optionally in the presence of an inert organic solvent at a temperature between 0° and 40° C., to give a thioether of the formula

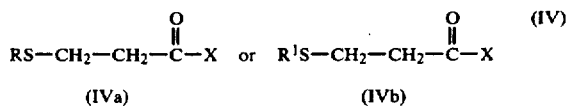

in which
X, R and R$^1$ have the meaning indicated above, and this intermediate product is reacted, optionally after isolation and optionally after activation, with a further, identical or different, mercaptan of the formula (III), optionally in the presence of an inert organic solvent at a temperature between 0° and 40° C.

When suitable reaction conditions are employed, it is possible, by using only one or two different mercaptans, to prepare compounds of the present invention in which the radicals R and R$^1$ are identical or different from one another.

For the preparation of compounds according to the invention which contain identical mercaptan radicals ($R = R^1$), a preferred process variant comprises reacting the acrylic acid derivatives of the formula (II), in which X represents a halogen atom, in particular a chlorine atom, direct with twice the equivalent amount of a mercaptan of the formula (III) in the presence of one equivalent of alkali metal hydroxide solution.

The compounds, according to the invention, of the formula (I) can also be obtained in a manner which is in itself known when a propionic acid derivative in which the carbon atom in the $\beta$-position has been activated, that is to say carried a nucleophilically replaceable substituent, such as Bromo, Chloro, Sulfuric acid ester or Arylsulfonic acid ester is used in place of the acrylic acid derivatives of formula (II), and the derivative of formula (IV) which are thus formed is further reacted in the manner indicated above.

Inert organic solvents which can be used are preferably cyclic ethers (such as dioxane or tetrahydrofurane), ketones (such as acetone), or dimethylformamide.

Activating agents and condensing agents are preferably dicycohexylcarbodiimide, carbonyldiimidazole, thionyl chloride or phosphoric acid halides (see Angew. Chem. 74. 407 (1962) and J. Amer Chem. Soc. 77, 1067 (1955))

Basic catalysts are preferably alkali metal hydroxides and amines, such as Alkylamines or Dialkylamines.

Alkali metal hydroxides are preferably sodium hydroxide and potassium hydroxide, especially sodium hydroxide, and, preferably, at most equimolar amounts, based on the compounds of the formula (II), are employed.

The acrylic acid derivatives of the formula (II) which can be employed according to the invention are known or can be prepared by known methods (see Beilstein E III 2, 1233 and J. Org. Chem. 9, 506 (1944)).

The mercaptans of the formula (III) which are used according to the invention are known or can be prepared by known methods (see, for example Org. Synth. Coll. Volume 3, 363).

The following mercaptans are mentioned by way of example:

2-Fluorobenzylmercaptan, boiling point$_{14}$ = 77°-81° C., 2,6-Dimethoxybenzylmercaptan, melting point = 78.5°-80.5° C.

and 3,4,5-Trimethoxybenzylmercaptan, waxy substance, $^1$H-NMR (CDCl$_3$), $\delta$ ppm = 1.75 (T, 1H); 3.62 (D, 2H); 3.78 (S, 9H); 6.45 (S, 2H).

Surprisingly, the compounds according to the invention display an advantageous antiphlogistic action coupled with very good tolerance. Moreover, the intensity of the odour of the sulphur compounds according to the invention is considerably less than that of the sulphur compounds known from the prior art. They can be processed and used with less odour nuisance and thus represent an enricyment of pharmacy.

As stated above, the invention also relates to the use in medicine of the compounds of the invention.

The present invention provides a pharmaceutical composition containing as active ingredient a compound of the invention in admixture with an inert pharmaceutical carrier, such as a solid or liquefied gaseous diluent, or a liquid diluent other than a solvent of a molecular weight less than 200 (preferably less than 350) except in the present of a surface active agent.

The invention further provides a pharmaceutical composition containing as active ingredient a compound of the invention in the form of a sterile solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in the Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active atents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. C$_{14}$-alcohol with C$_{16}$-fatty acid) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 10 mg to 1000 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally. Preferred pharmaceutical compositions and medicaments are therefore those adapted for administration such as parenteral administration. Administration in the method of the invention is preferably parenteral administration.

In general it has proved advantageous to administer orally amounts of from 100 to 4,000 mg/animal preferably 200 to 2,000 mg/animal per day, or to administer intramuscularly amount of from 10 to 1,500 mg/animal, preferably 50 to 800 mg/animal per day to achieve effective results. Where the active compound is administered in the form of several individual administrations, an individual administration preferably contains the active compound in amounts of from 10 to 300, preferably 50 to 200, mg/dose.

Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following examples illustrate the production of compounds of the present invention.

EXAMPLE 1

S-(3,4,5-Trimethoxybenzyl) 3-(3,4,5-trimethoxybenzylthio)-propionothioate 0.81 ml (10 mmoles) of acrylic acid chloride were added in portions, at room temperature, to a mixture of 4.28 g (20 mmoles) of 3,4,5-trimethoxybenzylmercaptan and 8 ml of 5% strength sodium hydroxide solution and the mixture was stirred until the exothermic reaction had ended. After diluting with water, the reaction mixture was extracted with ether, the ether phase was evaporated and the residue was subjected to chromatography from ether/diisopropyl ether (1:1) on a silica gel column. Melting point 88° to 89° C. Yield 1.55 g (32.1% of theory).

EXAMPLE 2

S-[2-(Diisopropylamino)-ethyl] 3-[2-(diisopropylamino)-ethylthio]-propionothioate 5.15 g (25 mmoles) of dicyclohexylcarbodiimide were added to a solution, which had been cooled to 0° C., of 1.8 g (25 mmoles) of acrylic acid and 8.07 g (50 mmoles) of 2-(diisopropylamino)-ethylmercaptan (obtained by extracting a solution of the hydrochloride, which had been rendered alkaline, with methylene chloride) and the mixture was stirred for 5 hours at room temperature and then left to stand overnight. After filtering off the dicyclohexylurea which had precipitated, the filtrate was evaporated in vacuo and the resulting oil was distilled twice in a bulb tube. Boiling point$_{0.05}$=200° C., yield 7.1 g (75.4% of theory).

EXAMPLE 3

S-(4-Fluorobenzyl) 3-benzylthiopropionothioate 6.18 g (30 mmoles) of dicyclohexylcarbodiimide in 20 ml of methylene chloride were added to a solution, which had been cooled to 0° C., of 5.9 g (30 mmoles) of 3-benzylthiopropionic acid and 4.26 g (30 mmoles) of 4-fluorobenzylmercaptan in 25 ml of methylene chloride, and the mixture was kept overnight at room temperature. After filtering off the dicyclohexylurea and stripping off the solvent, the crude product was purified, first by chromatography, on silica gel, from 1:2 methylene chloride/petroleum ether and then by distillation in a bulb tube.

Boiling point$_{0.05}$=215° to 240° C.,

Yield 7.4 g (77% of theory).

$^1$H-NMR (CDCl$_3$): δ ppm=2.65 (S, 4H); 3.60 (S, 2H); 3.97 (S, 2H); 6.90 (M, 4H); 7.25 (S, 5H).

EXAMPLE 4

S-(Furyl-2-methyl) 3-benzylthiopropionothioate was obtained analogously to Example 3:
Boiling point$_{0.05}$=210° to 220° C.,
Yield 73.6%.

$^1$H-NMR (CDCl$_3$): δ ppm=2.64 (S, 4H); 3.58 (S, 2H); 4.02 (S, 2H); 6.09 (M, 2H); 7.14 (broad S, 6H).

Compounds Nos. 5 to 30, which are listed in the table which follows, were prepared analogously to Example 1, and compounds Nos. 31 to 34 were prepared analogously to Example 2.

| Example No. | Compound | Yield % of theory | Boiling point (b.p.)/ melting point (m.p.) | $^1$H—NMR (CDCl$_3$), 60 MHz, Perkin Elmer R 24 A, δ ppm (TMS) |
|---|---|---|---|---|
| 5 | S—(3-Trifluoromethylbenzyl) 3-(3-trifluoromethylbenzylthio)-propionothioate | 40 | oil | 2.71 (S, 4H); 3.68 (S, 2H); 4.08 (s, 2H); 7.25–7.62 (M, 8H) |
| 6 | S—(3,4-Dichlorobenzyl) 3-(3,4-dichlorobenzylthio)-propionothioate | 58 | oil | 2.68 (S, 4H); 3.58 (S, 2H); 3.98 (S, 2H); 6.57–7.36 (M, 6H) |
| 7 | S—(4-Methoxybenzyl) 3-(4-methoxybenzylthio)-propionothioate | 29.7 | m.p. = 41–42° C. | 2.62 (S, 4H); 3.55 (S, 2H); 3.63 (S, 6H); 3.97 (S, 2H); 6.90 Q, 8H) |
| 8 | S—(3-Methylbenzyl) 3-(3-methylbenzylthio)-propionothioate | 18.2 | oil | 2.24 (S, 6H); 2.68 (S, 4H); 3.60 (S, 2H); 4.01 (S, 2H); 7.02 (S, 8H) |
| 9 | S—(Furyl-2-methyl) 3-(furyl-2-methylthio)-propionothioate | 23 | oil | 2.72 (S, 4H); 3.65 (S, 2H); 4.10 (S, 2H); 6.05–6.3 (M, 4H); 7.15–7.32 (M, 2H) |
| 10 | S—(4-Chlorobenzyl) 3-(4-chlorobenzylthio)-propionothioate | 60.6 | m.p. = 41–42° C. | 2.65 (S, 4H); 3.55 (S, 2H); 3.97 (2H); 7.12 (S, 8H) |
| 11 | S—(2,6-Dichlorobenzyl) 3-(2,6-dichlorobenzylthio)-propionothioate | 38.6 | oil | 2.85 (S, 4H); 3.98 (S, 2H); 4.41 (S, 2H); 6.8–7.3 (M, 6H) |
| 12 | S—(3,4,5-Trimethoxybenzyl) 3-(3,4,5-trimethoxybenzylthio)-propionothioate | 32.1 | m.p. = 88–89° C. | 2.73 (S, 4H); 3.61 (S, 2H); 3.76 (S, 18H); 4.0 (S, 2H); 6.41 (S, 2H); 6.45 (S, 2H) |
| 13 | S—(4-Fluorobenzyl) 3-(4-fluorobenzylthio)-propionothioate | 74.9 | oil | 2.69 (S, 4H); 3.58 (S, 2H); 3.99 (S, 2H); 6.6–7.3 (M, 8H) |
| 14 | S—(Diphenylmethyl) 3-(diphenylmethylthio)-propionothioate | 14.9 | oil | 2.61 (S, 4H); 5.01 (S, 1H); 5.83 (S, 1H); 6.95–7.4 (M, 20H) |
| 15 | S—(Pyridyl-2-methyl) 3-(pyridyl-2-methylthio)-propionothioate | 49.4 | oil | 2.5–3.4 (M, 8H); 6.5–8.0 (M, 6H); 8.3 (M, 2H) |
| 16 | S—(2,6-Dimethoxy) 3-(2,6-dimethoxybenzylthio)-propionothioate | 18.1 | m.p. = 81–83° C. | 2.73 (S, 4H); 3.71 (S, 14H); 4.15 (S, 2H); 6.4 (D, 4H); 6.82–7.18 (M, 2H) |
| 17 | S—(1-Phenylpropyl) 3-(1-phenylpropylthio)-propionothioate | 7 | oil | 0.85 (T, 6H); 1.45–2.1 (M, 4H); 2.51 (S, 4H); 3.52–3.68 (T, 1H); 4.38 (T, 1H); 7.15 (S, 10H) |
| 18 | S—(Thienyl-2-methyl) 3-thienyl-2-methylthio)-propionothioate | 44.5 | oil | 2.71 (S, 4H); 3.81 (S, 2H); 4.22 (S, 2H); 6.50–7.32 (M, 6H) |
| 19 | S—(1-Phenylethyl) 3-(1-phenylethylthio)-propionothioate | 22.7 | b.p.$_{0.035}$ = 250° C. (bulb tube) | 1.6 (T, 6H); 2.55 (S, 4H); 3.85 (Q, 1H); 4.65 (Q, 1H); 7.28 (S, 10H) |
| 20 | S—(4-Nitrobenzyl) 3-(4-nitrobenzylthio)-propionothioate | 24.2 | m.p. = 60–61° C. | 2.72 (S, 4H); 3.71 (S, 2H); 4.11 (S, 2H); 7.16–8.2 (M, 8H) |
| 21 | S—(2-Trifluoromethylbenzyl) 3-(2-trifluoromethylbenzylthio)-propionothioate | 47.5 | b.p.$_{0.035}$ = 240–50° C. (bulb tube) | 2.7 (S, 4H); 3.66 (S, 2H); 4.07 (S, 2H); 7.2–7.55 (M, 8H) |
| 22 | S—(4-Methylbenzyl) 3-(4-methylbenzylthio)-propionothioate | 31.3 | b.p.$_{0.035}$ = 250° C. (bulb tube) | 2.23 (S, 6H); 2.63 (S, 4H); 3.57 (S, 2H); 3.98 (S, 2H); 7.01 (S, 8H) |
| 23 | S—(Naphthyl-2-methyl) 3-(naphthyl-2-methylthio)-propionothioate | 42.3 | waxy substance | 2.66 (S, 4H); 3.97 (S, 2H); 4.42 (S, 2H); 6.99–7.98 (M, 14H) |
| 24 | S—(4-Benzyloxybenzyl) 3-(4-benzyloxy-benzylthio)-propionothioate | 38.8 | m.p. = 96–98° C. | 2.67 (S, 4H); 3.56 (S, 2H); 3.98 (S, 2H); 4.95 (S, 4H); 6.93 (Q, 8H); 7.23 (S, 10H) |
| 25 | S—(3-Fluorobenzyl) 3-(3-fluorobenzylthio)-propiono- | 23.1 | b.p.$_{0.05}$ = 245–50° C. | 2.67 (S, 4H); 3.56 (S, 2H); 3.98 (S, 2H); 6.6–7.35 (M, 8H) |

-continued

| Example No. | Compound | Yield % of theory | Boiling point (b.p.)/ melting point (m.p.) | $^1$H—NMR (CDCl$_3$), 60 MHz, Perkin Elmer R 24 A, δ ppm (TMS) |
|---|---|---|---|---|
| | thioate | | (bulb tube) | |
| 26 | S—(2-Fluorobenzyl) 3-(2-fluorobenzylthio)-propionothioate | 40.4 | b.p.$_{0.05}$ = 235° C. (bulb tube) | 2.70 (S, 4H); 3.64 (S, 2H); 4.05 (S, 2H); 6.65–7.35 (M, 8H) |
| 27 | S—(2-Phenylisopropyl) 3-(2-phenylisopropylthio)-propionothioate | 36.3 | oil | 1.1–1.35 (2D, 6H); 2.4–3.1 (M, 9H); 3.4–3.95 (M, 1H); 7.1 (S, 10H) |
| 28 | S—(2-Phenoxyethyl) 3-(2-phenoxyethylthio)-propionothioate | 18.4 | b.p.$_{0.035}$ = 240–50° C. (bulb tube) | 2.70–3.05 (M, 6H); 3.22 (T, 2H); 3.86–4.23 (M, 4H); 6.68–7.33 (M, 10H) |
| 29 | S—(2-Cyclohexylethyl) 3-(2-cyclohexylethylthio)-propionothioate | 16.1 | b.p.$_{0.035}$ = 240–50° C. | 0.51–1.95 (M, 26H); 2.46 (T, 2H); 2.74 (S, 4H); 2.82 (T, 2H) |
| 30 | S—(adamant-1-yl) 3-(adamant-1-yl-thio)-propionothioate | 30.7 | m.p. = 108–110° C. | 1.53–2.32 (M, 30H); 2.63 (S, 4H) |
| 31 | S—(2-Phenylethyl) 3-(2-phenylethylthio)-propionothioate | 34.3 | b.p.$_{0.035}$ = 250° C. (bulb tube) | 2.67 (s, 4H); 2.6–3.15 (M, 8H); 7.05 (S, 10H) |
| 32 | S—[2-(Dimethylamino)-ethyl] 3-[2-(dimethylamino)-ethylthio]-propionioate | 30.4 | b.p.$_{0.035}$ = 190–200° C. (bulb tube) | 1.72 (M, 4H); 2.18 (S, 12H); 2.2–2.5 (M, 4H); 2.7–3.01 (M, 4H) |
| 33 | S—[2-Diethylamino] 3-[2-(diethylamino)-ethylthio]-propionothioate | 38.7 | b.p.$_{0.035}$ = 165–70° C. (bulb tube) | 1.00 (T, 12H); 2.50 (Q, 8H); 2.58 (S, 4H); 260–3.02 (M, 4H) |
| 34 | S—[2-(Diisopropylamino)-ethyl] 3-[2-diisopropylamino)-ethylthio]-propionothioate | 75.4 | b.p.$_{0.035}$ = 200° C. (bulb tube) | 1.01 (D, 24H); 2.50–3.20 (M, 16H) |

The present invention also comprises pharmaceutically acceptable bioprecursors of the active compounds of the present invention.

For the purpose of this specification the term 'pharmaceutically acceptable bioprecursor' of an active compound of the invention means a compound having a structural formula different from the active compound but which nonetheless, upon administration to a warm-blooded animal is converted to the patient's body to the active compound.

What is claimed is:

1. A compound which is an S-alkyl 3-alkylthiopropionothioates of the formula

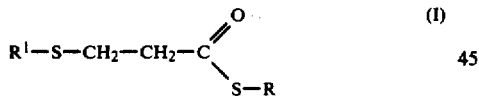

in which
R and R$^1$ are identical or different and each represents a substituted straight-chain or branched alkyl radical, which is substituted by amino, alkylamino, dialkylamino, aryl, aryloxy, or hetero-aryl, the said aryl and hetero-aryl radicals in turn being optionally substituted by 1, 2 or 3 identical or different substituents selected from halogen, alkyl, alkoxy, trifluoromethyl, nitro, aralkoxy or aryloxy, or represent a cyclic alkyl radical.

2. A compound according to claim 1 in which
R and R$^1$ are identical or different and each represents a substituted straight-chain or branched alkyl radical with 1 to 10 carbon atoms, the alkyl radical being substituted by amino or alkylamino or dialkylamino, each with 1 to 4 carbon atoms in the alkyl groups or by phenyl, naphthyl, phenoxy or naphthoxy, or by hetero-aryl with 5-membered to 7-membered rings which contain one or two oxygen, sulphur or nitrogen atoms as the hetero-atoms, the said phenyl, phenoxy and hetero-aryl radicals in turn being optionally substituted by 1, 2 or 3 identical or different substituents selected from halogen, trifluoromethyl, nitro, phenoxy, benzyloxy and alkyl or alkoxy, each with 1 to 4 carbon atoms, or represents a mono-, di-, tri- or tetracyclic alkyl radical with 5 to 10 carbon atoms.

3. A compound according to claim 1 in which
R and R$^1$ are identical or different and each represents a substituted straight-chain or branched alkyl radical with 1 to 6 carbon atoms or represents an adamantyl radical, the alkyl radical being substituted by amino or alkylamino or dialkylamino, each with 1 to 4 carbon atoms in the alkyl radicals, or by phenyl, naphthyl or phenoxy radicals or 5-membered to 6-membered hetero-aryl radicals which contain an oxygen, sulphur or nitrogen atom as the hetero-atom, the said phenyl and phenoxy radicals being optionally substituted by 1 or 2 identical or different substituents from the group comprising halogen, trifluoromethyl, nitro, benzyloxy or alkyl with 1 to 2 carbon atoms or alkoxy with 1 to 2 carbon atoms.

4. A compound according to claim 1 which is S-(adamant-1-yl) 3-(adamantly-1-thio)-propionothioate.

5. A compound according to claim 1 which is S-(2,6-dichlorobenzyl) 3-(2,6-dichlorobenzylthio)-propionothioate.

6. A compound according to claim 1 which is S-thienyl-2-methyl 3-(thienyl-2-methylthio)-propionothioate.

7. A compound according to claim 1 which is S-(3-fluorobenzyl) 3-(3-fluorobenzylthio)-propionothioate.

8. A compound according to claim 1 which is S-(2-phenylisopropyl) 3-(2-phenylisopropylthio)-propionothioate.

9. A compound according to claim 1 which is S-(4-Fluorobenzyl) 3-(4-fluoro-benzylthio)-propionothioate.

10. A pharmaceutical composition containing as an active ingredient an antiinflammatory effective amount of a compound according to claim 1 in admixture with an inert pharmaceutical carrier.

11. A pharmaceutical composition according to claim 10 in the form of a sterile or physiologically isotonic aqueous solution.

12. A composition according to claim 10 or 11 containing from 0.5 to 95% by weight of the said active ingredient.

13. A medicament in dosage unit form comprising an antiinflammatory effective amount of a compound according to claim 1 together with an inert pharmaceutical carrier.

14. A medicament of claim 13 in the form of tablets, pills, dragees, capsules, ampoules, or suppositories.

15. A method of combating inflammatory processes in warm-blooded animals which comprises administering to the animals an antiinflammatory effective amount of an active compound according to claim 1 either alone or in admixture with a diluent or in the form of a medicament.

16. A method according to claim 15 in which the active compound is administered in an amount of 10 to 1000 mg per kg body weight per day.

17. A method according to claim 15 or 16 in which the active compound is administered parenterally.

* * * * *